United States Patent [19]
Hirschmann et al.

[11] Patent Number: 5,886,046
[45] Date of Patent: Mar. 23, 1999

[54] DICARBONYL-CONTAINING COMPOUNDS

[75] Inventors: Ralph F. Hirschmann, Blue Bell; Amos B. Smith, III, Merion; Paul Sprengeler, Philadelphia; Wenqing Yao, Lansdowne; Paul Anderson, Lansdale, all of Pa.

[73] Assignee: The Trustees of the University of Pennsylvania, Philadelphia, Pa.

[21] Appl. No.: 588,763

[22] Filed: Jan. 19, 1996

[51] Int. Cl.$^6$ .................. A61K 31/165; C07C 233/05
[52] U.S. Cl. .................. 514/617; 514/375; 514/407; 514/485; 514/619; 514/620; 514/621; 514/622; 548/218; 548/375.1; 560/27; 564/155; 564/156; 564/165; 564/169; 564/174
[58] Field of Search .................. 564/165, 169, 564/174, 155, 156; 560/27; 514/619, 620, 621, 622, 485, 616, 617, 375, 407; 548/218, 375.1

[56] References Cited

PUBLICATIONS

Slee et al. J. Am. Chem. Soc., 1995, 117, 11867–11878.
Smith et al, J. Biol. Chem. vol. 267, 1992, 5599–5607.
Askin et al., "Highly Diastereoselective Alkylations of Chiral Amide Enolates: New Routes to Hydroxyethylene Dipeptide Isostere Inhibitors of HIV–1 Protease", *J. Org. Chem.*, 1992, 57, 2771–2773.
Atherton et al., "The Fluorenylmethoxycarbonyl Amino Protecting Group", *The Peptides*, Academic Press, Inc., 1987, vol. 9, Chp. 1, 1–38.
Baker et al., "Active–Site–Directed Irreversible Inhibitors", *J. Theoret Biol.*, 1962, 3(459), 122–155.
Heimbach et al., "Affinity Purification of the HIV–1 Protease", *Biochem. Biophys. Res. Commun.*, 1989, 164(3), 955–960.
Schaeffer, "Factors in the Design of Reversible and Irreversible Enzyme Inhibitors", Chapter 2, 130–160, 1971.
Thompson et al., "Synthesis and Antiviral Activity of a Series of HIV–1, Protease Inhibitors with Functionality Tethered to the $P_1$ or $P_1$, Phenyl Substituents: X–ray Crystal Structure Assisted Design", *J. Med. Chem.*, 1992, 35, 1685–1701.
Tipper et al., "Mechanism of Action of Penicillins: A Proposal Based on Their Structural Similarity to Acyl–D–Alanyl–D–Alanine", *Microbiology*, 1965, 54, 1133–1141.
Toi et al., "Studies on the Chemical Modification of Arginine: I. The Reaction of 1,2–Cyclohexanedione with Arginine and Arginyl Residues of Proteins", *J. Biol. Chem.*, 1967, 242(5), 1036–1043.
Veber et al., "Isonicotinyloxycarbonyl, a Novel Amino Protecting Group for Peptide Synthesis", *J. Org. Chem.*, 1977, 42(20), 3286–3288.
Greene and Wuts, "Protective Groups in Organic Synthesis", 2nd Ed., John Wiley & Sons, New York, 1991.

*Primary Examiner*—Shailendra Kumar
*Attorney, Agent, or Firm*—Woodcock Washburn Kurtz Mackiewicz & Norris LLP

[57] ABSTRACT

This invention relates to chemical compounds that contain adjacent carbonyl groups, which effectively inhibit the biological, chemical, and/or physical properties of enzymes and other medicinally-significant proteins. In particular, the invention relates to dicarbonyl compounds that are capable of acting as enzyme inhibitors, including irreversible inhibitors of HIV-1 protease.

14 Claims, 10 Drawing Sheets

ACTIVE SITES OF HIV-1 PROTEASE DOCKED WITH DESIGNED INHIBITOR

THE CONVERSION OF ALKYNE TO α-DIKETONE 1, 1-BROMO-2-BUTYNE
K₂CO₃, DMF
————————————→
2, TES-Cl, IMIDAZOLE, DMF
86% IN TWO STEPS.

RuO₂, NaIO₄
——————————
CH₃CN/CHCl₃/H₂O
(2:2:3)
48%

THE COMPLETION OF THE SYNTHESIS OF COMPOUND 4

DICARBONYL-CONTAINING COMPOUNDS

GOVERNMENT SUPPORT

Certain of the inventors have been supported by National Institutes of Health (Institute of General Medicine) GM-50581.

FIELD OF THE INVENTION

This invention relates to chemical compounds that contain adjacent carbonyl groups, particularly those that effectively inhibit the biological, chemical, and/or physical properties of enzymes and other medicinally-significant proteins. In particular, the invention relates to compounds that are capable of acting as enzyme inhibitors, including irreversible inhibitors of HIV-1 protease.

BACKGROUND OF THE INVENTION

Proteins, acting either directly or through their enzymatic functions, are implicated in many diseases in humans and other mammals. The inhibition of disease causing or disease potentiating proteins is, therefore, one major goal of medicinal chemistry. Known enzyme inhibitors, however, tend to have poor oral bioavailability and a short biological half-life, particularly inhibitors for HIV-1 protease.

There remains a need in the art for compounds which effectively inhibit the biological, chemical, and/or physical properties of enzymes and other medicinally-significant proteins. The present invention addresses these as well as other needs.

SUMMARY OF THE INVENTION

The present invention provides novel dicarbonyl-containing compounds. These compounds are useful, inter alia, in modulating the activity of enzymes and other proteins.

In one aspect, the present invention provides compounds of the general formula:

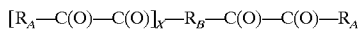

[$R_A$—C(O)—C(O)]$_x$—$R_B$—C(O)—C(O)—$R_A$ wherein $R_A$ is $R_{A1}$, $OR_{A2}$, $NHR_{A2}$, where $R_{A1}$ is H, alkyl having 1 to about 12 carbon atoms or haloalkyl having 1 to about 12 carbon atoms and $R_{A2}$ is H or alkyl having 1 to about 12 carbon atoms; $R_B$ is a moiety that binds a protein; and x is 0 or 1. In preferred embodiments, $R_A$ is methyl or trifluoromethyl and $R_B$ has the general formula:

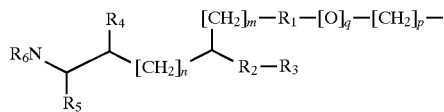

wherein:
  $R_1$ is aryl having 5 to 14 carbon atoms;
  $R_2$ and $R_3$ are defined such that:
    (a) $R_2$ is C(O)—NH, —CH=CH—, a pyrrolinone ring, —SO$_2$-, —P(O) (OR')O—, —P(O) (OR')NH,—CH$_2$NH, wherein R' is H or alkyl having 1 to about 5 carbon atoms; and
    $R_3$ is indolyl, aryl having about 5 to about 14 carbon atoms, or alkyl having 1 to about 12 carbon atoms; or
    (b) $R_2$ is C(O); and
    $R_3$ is NH—CH($R_7$)—C(O) OH wherein $R_7$ is an amino acid side chain;

$R_4$ is OH, —CH(OH)—, —CH(OH)CH(OH)—, CH$_2$NH—, —SO$_2$—, —P(O) (OR')O—, —P(O) (OR')NH—, or —C(O)CF$_2$;
  $R_5$ is aryl having about 5 to about 14 carbon atoms or an amino acid side chain;
  $R_6$ is an amine protecting group or has the structure $R_8$—C(O)—wherein $R_8$ is alkyl having 1 to about 12 carbon atoms or aryl having about 5 to about 14 carbon atoms;
  n is 1–5;
  m is 1–10;
  q is 0 or 1; and
  p is 1–10.

The invention further provides methods for producing a prophylactic or therapeutic response in a mammal by administering to the mammal a pharmaceutically effective amount of one or more compounds of the invention. In preferred embodiments, compounds of the invention are used in mammals to inhibit the activity of a mammalian enzyme. In yet other aspects of the invention, methods of utilizing the novel compounds of the invention in diagnostic techniques are presented.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
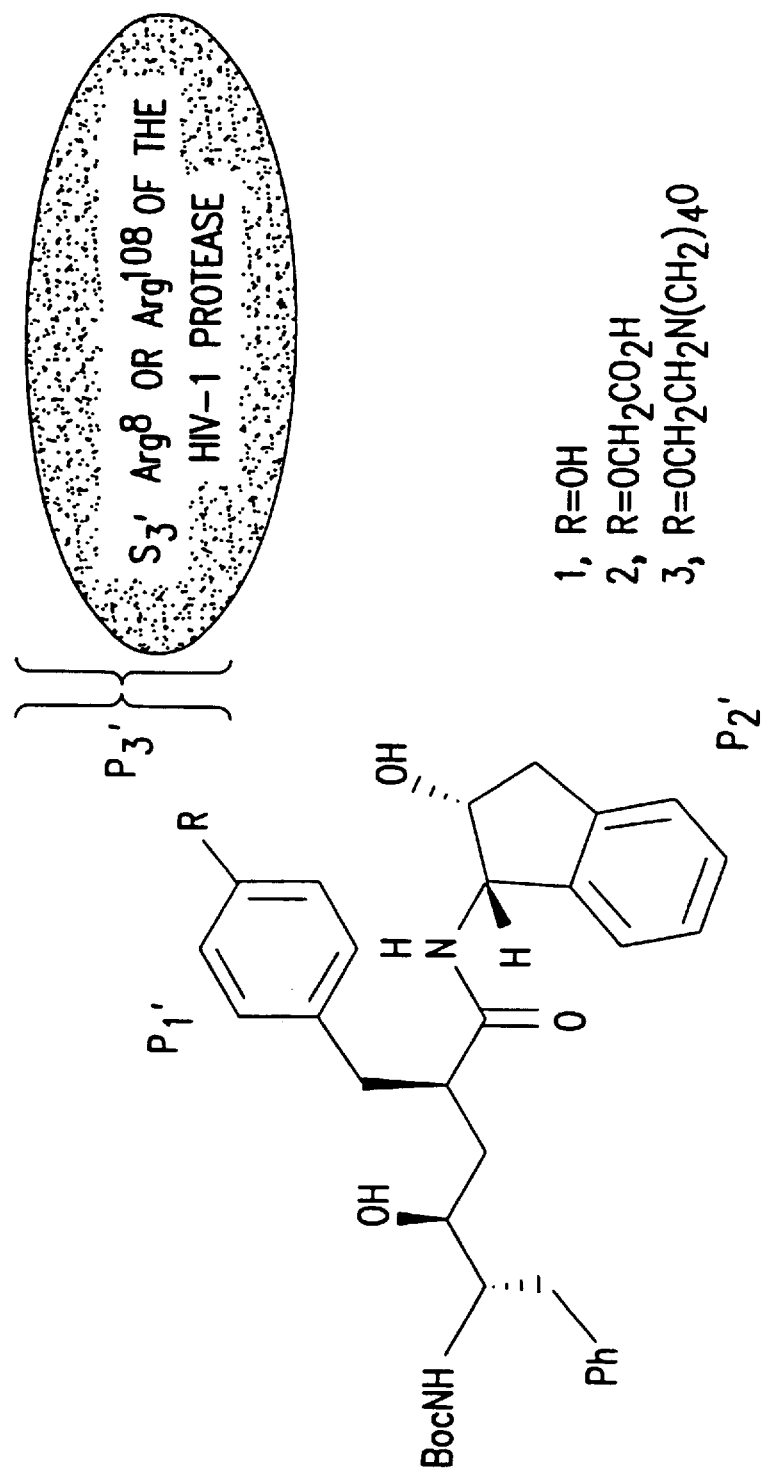
FIG. 1 depicts the binding of arginine residues of HIV-1 protease with a protease inhibitor. Both the S3 and S3' pockets of the HIV-1 protease are flanked by a pair of arginine residues (Arg$^8$ and Arg$^{108}$).
Figure 2:
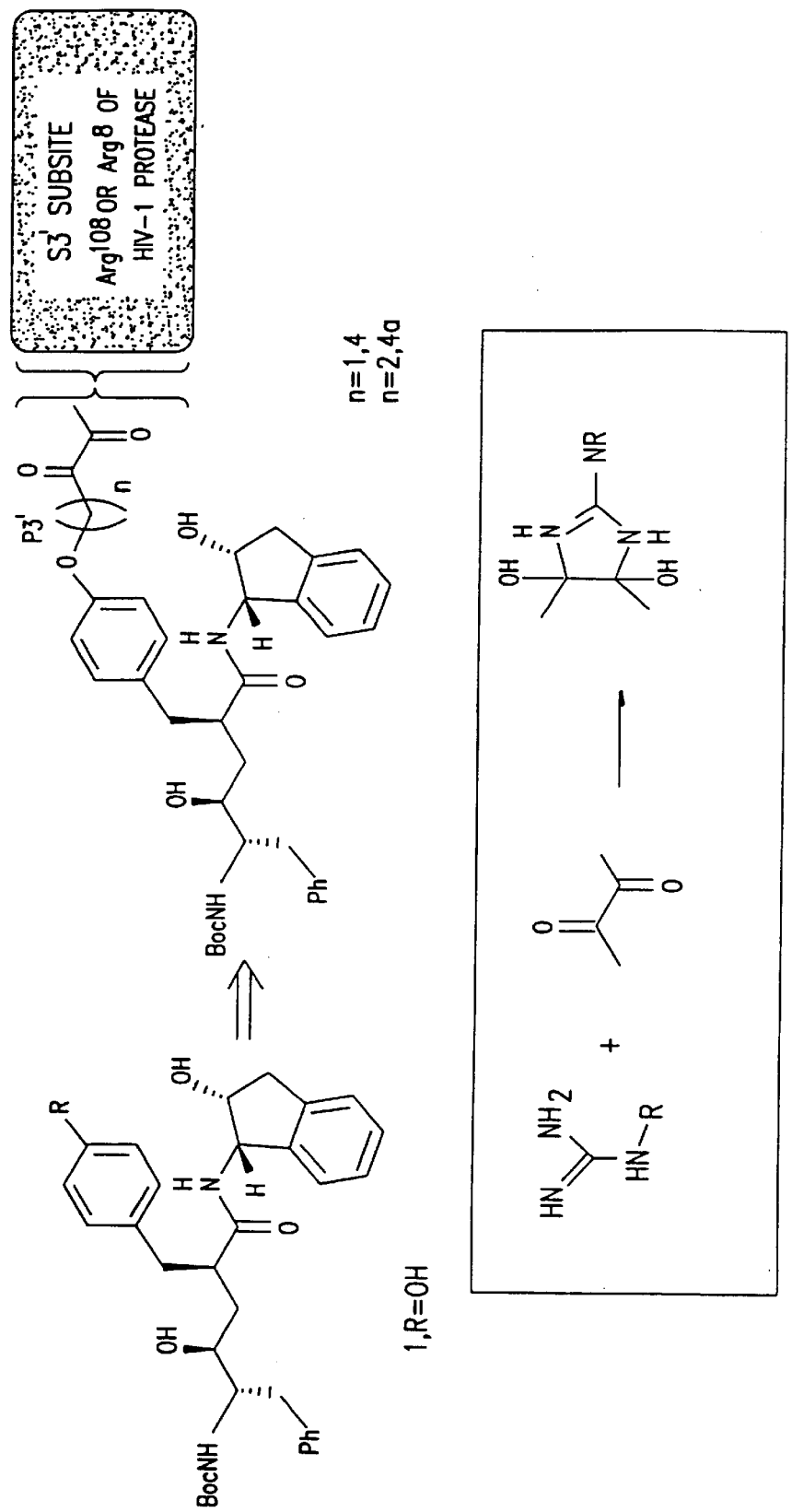
FIG. 2 depicts the synthesis and behavior of an irreversible inhibitor of the invention. In a preferred embodiment, an irreversible inhibitor (compound 1 of FIG. 1) can be turned into an active site directed irreversible inhibitor by incorporating an α-diketone moiety at the P3' position (compound 4). Once the compound binds to the active site of the protease, the α-diketone group then reacts in situ with the guanidino group of Arg$^8$ and Arg$^{108}$ of the HIV-1 protease to form a covalent bond. (See Toi, K.; Bynum, E.; Norris, E.; Itano, H., J. Biol. Chem. 1967, 242, 1036).
Figure 3:
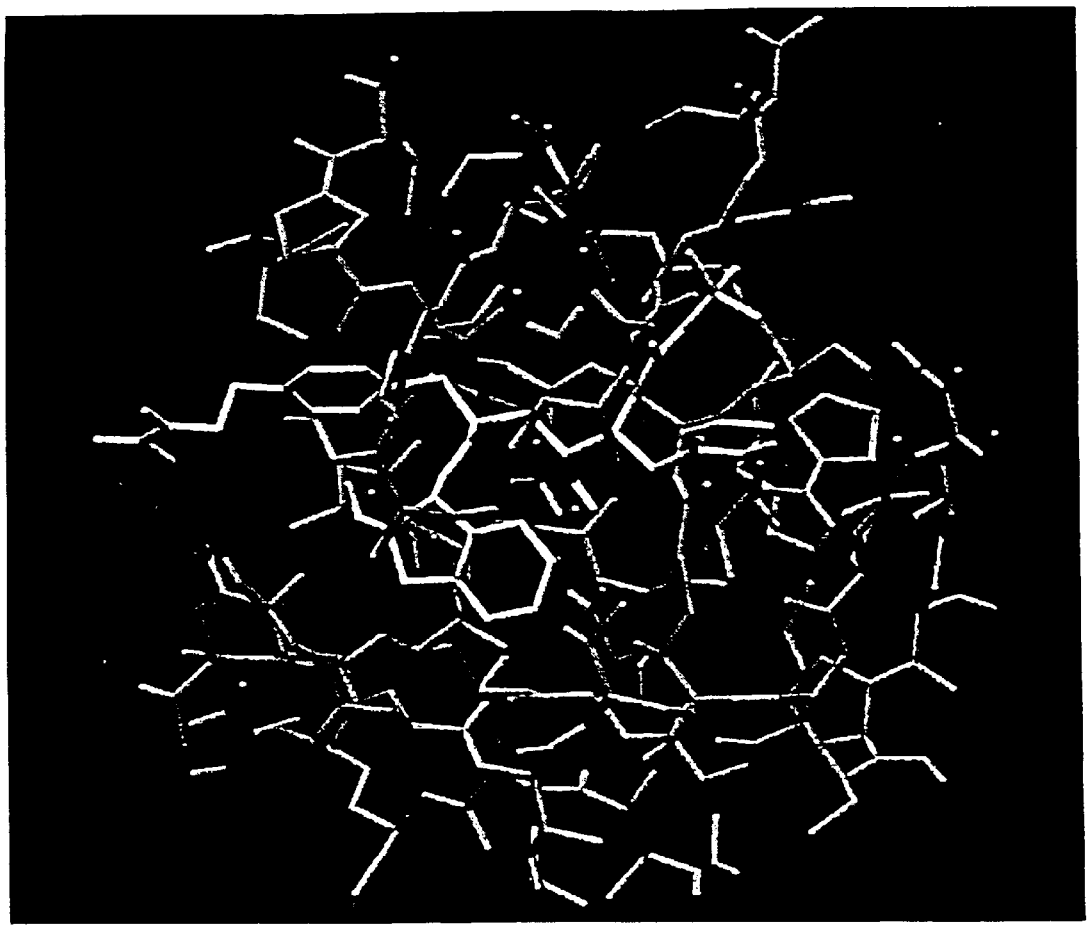
FIG. 3 depicts the active sites of HIV-1 protease docked with a design inhibitor of the invention.

As used herein, the term "alkyl" refers to radicals that are formed from the loss of a hydrogen from an alkane ($C_nH_{2n+2}$). The alkyl compounds may be straight or branched chain compounds, cyclic or acyclic, and further substituted with hetero atoms (i.e., O, S, N), halogen atoms, or other aliphatic groups. Also included within this definition are structural isomers (i.e., chain isomers, position isomers, and functional isomers) and stereoisomers (i.e., enantiomers and diastereomers). Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 12 carbon atoms.

As used herein, the term "aryl" refers to aromatic groups having 3 to about 20 carbon atoms, preferably from 5 to about 14 carbon atoms, including, for example, imidazolyl, naphthyl, phenyl, pyridyl, pyrimidinyl, and xylyl groups, and substituted derivatives thereof.

The phrase "dicarbonyl residue," as used herein, refers to moieties having two carbonyl (i.e., C(O)) groups, particularly adjacent carbonyl groups.

The term "amino acid," as used herein, is intended to include all naturally-occurring and synthetic amino acids known in the art. As will be recognized, amino acids have both C-terminal and N-terminal ends, either of which can be covalently bound to the compounds of the invention. In general, amino acids have the structure $H_2N—CH(R_7)—C(O)OH$ where $R_7$ is the amino acid side chain. Representative, naturally-occurring side chains are shown in Table 1.

Protecting groups according to the invention are chemical functional groups used for blocking reactive sites on a multifunctional molecule to prevent such reactive sites from taking part in a chemical reaction. Protecting groups are known per se as chemical functional groups that can be selectively appended to and removed from a functionality, such as amine groups, present in a chemical compound to render such functionality inert to chemical reaction conditions to which the compound is exposed. (See, e.g., Greene and Wuts, Protective Groups in Organic Synthesis, 2d. edition, John Wiley & Sons, New York, 1991). Numerous amine protecting groups are known in the art, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (See, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid. Carboxyl protecting groups also are known, including lower (i.e., $C_1–C_7$) alkyl esters and benzyl esters. Preferred carboxyl protecting groups are stable to acid but can be removed with base.

Figure 4:
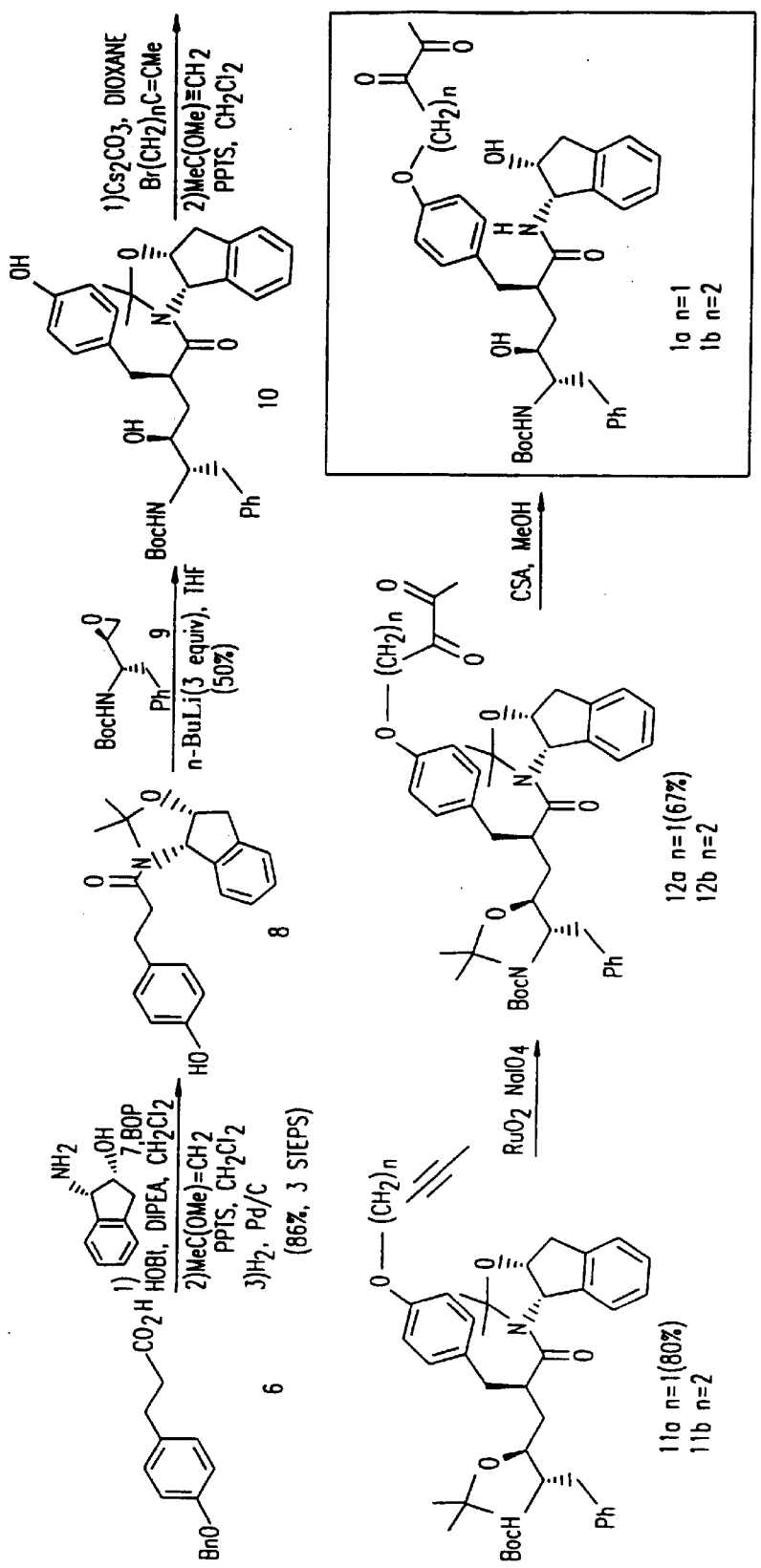
FIG. 4 depicts a synthetic scheme for making compounds of the invention (1a and 1b) where the dicarbonyl moiety is attached to the para position of the phenyl moiety.

In preferred embodiments, compounds of the invention are prepared according to a reaction scheme such as generally shown in FIG. 4. The synthesis of compounds 1a and 1b begin with the efficient coupling (86% for 3 steps) of acid 6 (available in two steps from 3–4(hydroxyphenyl)propionic

TABLE 1

$CH_3—$
$HO—CH_2—$
$C_6H_5—CH_2—$
$HO—C_6H_5—CH_2—$

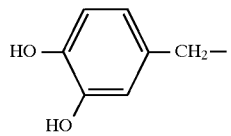

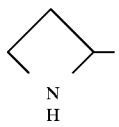

$CH_3—CH_2—S—CH_2—CH_2—$
$HO—CH_2—CH_2—$
$CH_3—CH_2(OH)—$
$HO_2C—CH_2—NH_2C(O)—CH_2—$

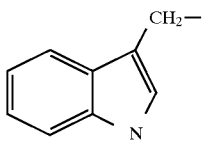

$HCO_2—CH_2—CH_2—$
$NH_2C(O)—CH_2—CH_2—$
$(CH_3)_2—CH—$
$(CH_3)_2—CH—CH_2—$
$CH_3—CH_2—CH_2—$
$H_2N—CH_2—CH_2—CH_2—$
$H_2N—C(NH)—NH—CH_2—CH_2—CH_2—$
$H_2N—C(O)—NH—CH_2—CH_2—CH_2—$
$CH_3—CH_2—CH(CH_3)—$
$CH_3—CH_2—CH_2—CH_2—$
$H_2N—CH_2—CH_2—CH_2—CH_2—$

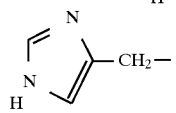

$HS—CH_2—$
$HO_2C—CH(NH_2)—CH_2—S—S—CH_2—$
$CH_3—CH_2—$
$CH_3—S—CH_2—CH_2—$

Preferred side chains include $C_6H_5—CH_2—$; $(CH_3)_2—CH—$; and $(CH_3)_2—CH—CH_2—$.

Figure 5:
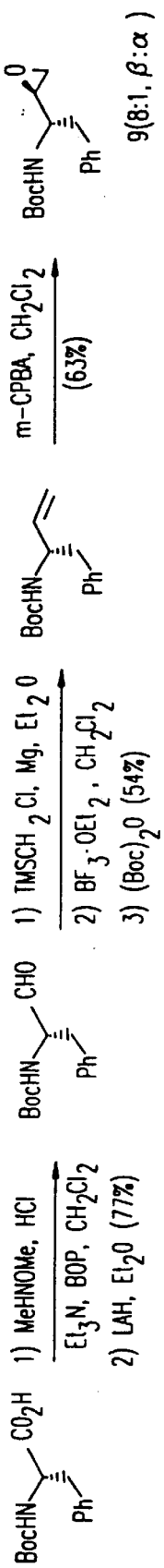
FIG. 5 depicts a synthetic scheme for an epoxide 9, useful in synthesizing compounds of the invention.

Peptides according to the invention are linear, branched, or cyclic chemical structures containing at least two covalently bound amino acids. Like individual amino acids, peptides can be incorporated into the compounds of the invention through C-terminal or N-terminal positions. Proteins according to the invention are compounds containing greater than five consecutive, covalently bound amino acids.

acid (Aldrich)) and amino alcohol 7. After protection and hydrogenation, coupling of the enolate of 8 with epoxide 9 (Thompson, W. J., et al., *J. Med. Chem.* 2992, 35, 1685) provides 10, the diketone moiety masked as an acetylene is attached to compound 10. One preferred synthetic scheme for epoxide 9 is shown in FIG. 5. Alkylation of the phenolic hydroxyl with 1-bromo-2-butyne or 1-bromo-3-pentyne followed by protection as the acetonide provides hla and lib, respectively. Oxidation of the alkyne to the diketone employing a Seebach protocol provides compounds 1a or 1b after final deprotection.

Figure 6:
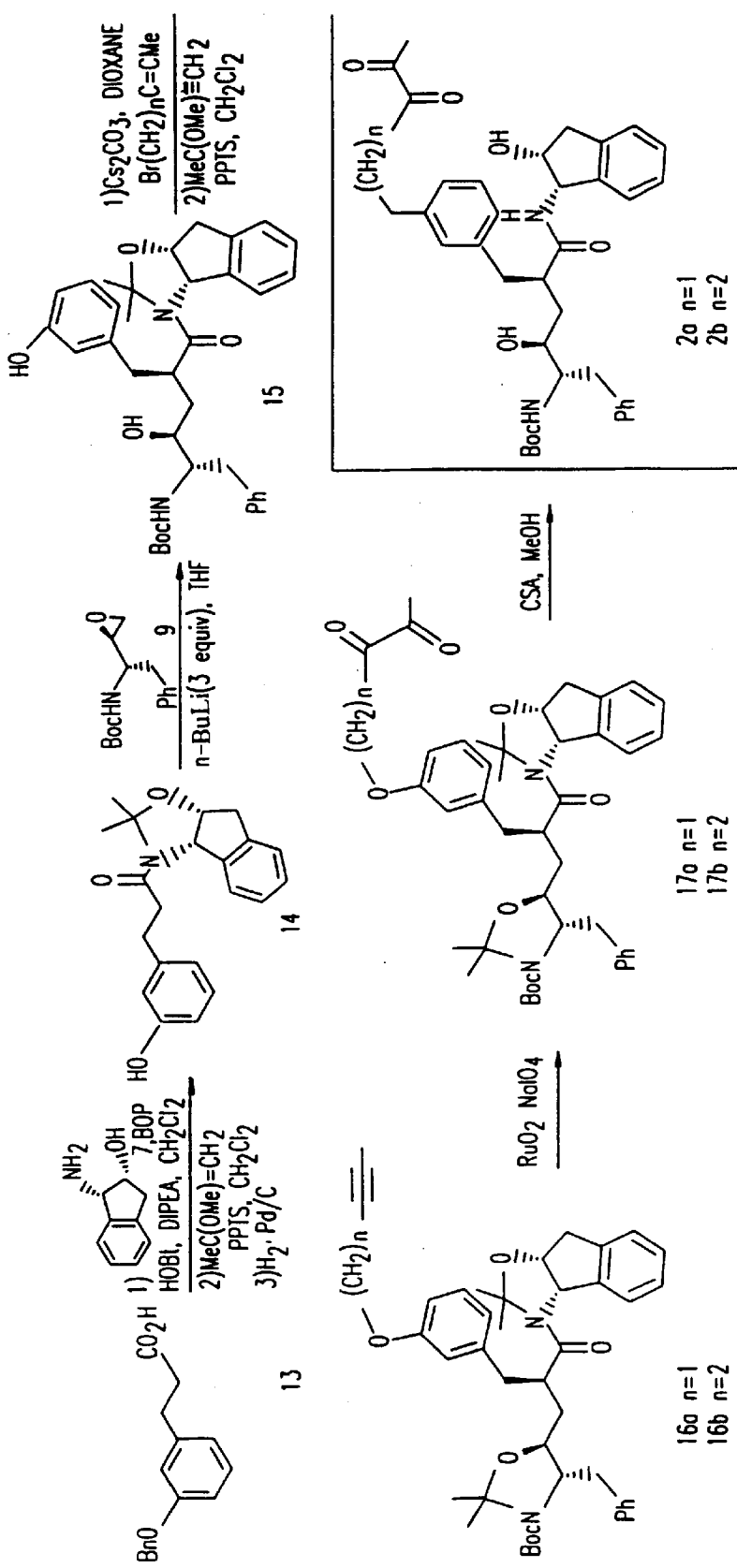
FIG. 6 depicts a synthetic scheme for compounds of the invention (2a and 2b) where the dicarbonyl moiety is attached to the meta position of the phenyl moiety.
Figure 7:
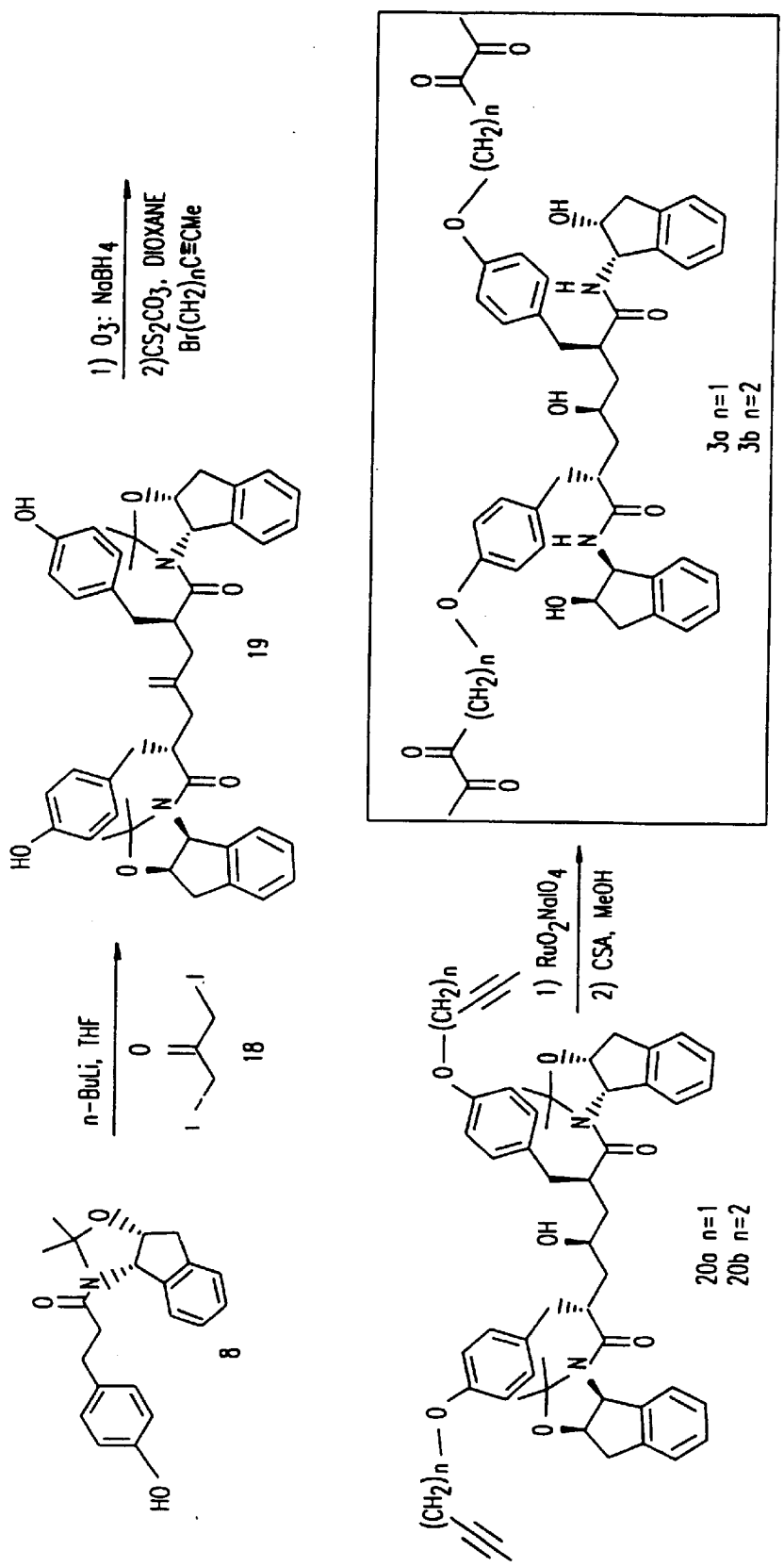
FIG. 7 depicts a synthetic scheme for compounds of the invention (3a and 3b) where there is more than one dicarbonyl moiety attached to a protein binding moiety.

Further compounds of the invention can be prepared according to the synthetic scheme shown in FIG. 6. The syntheses of 2a and 2b are essentially the same as for 1a,b except the initial coupling employs acid 13 (available from 3-hydroxybenzaldehyde (Aldrich)). The remainder of the synthesis follows the scheme as discussed above in connection with 1a and 1b. Still further representative synthetic procedures are shown in FIG. 7 for compounds 3a and 3b.

Figure 8:
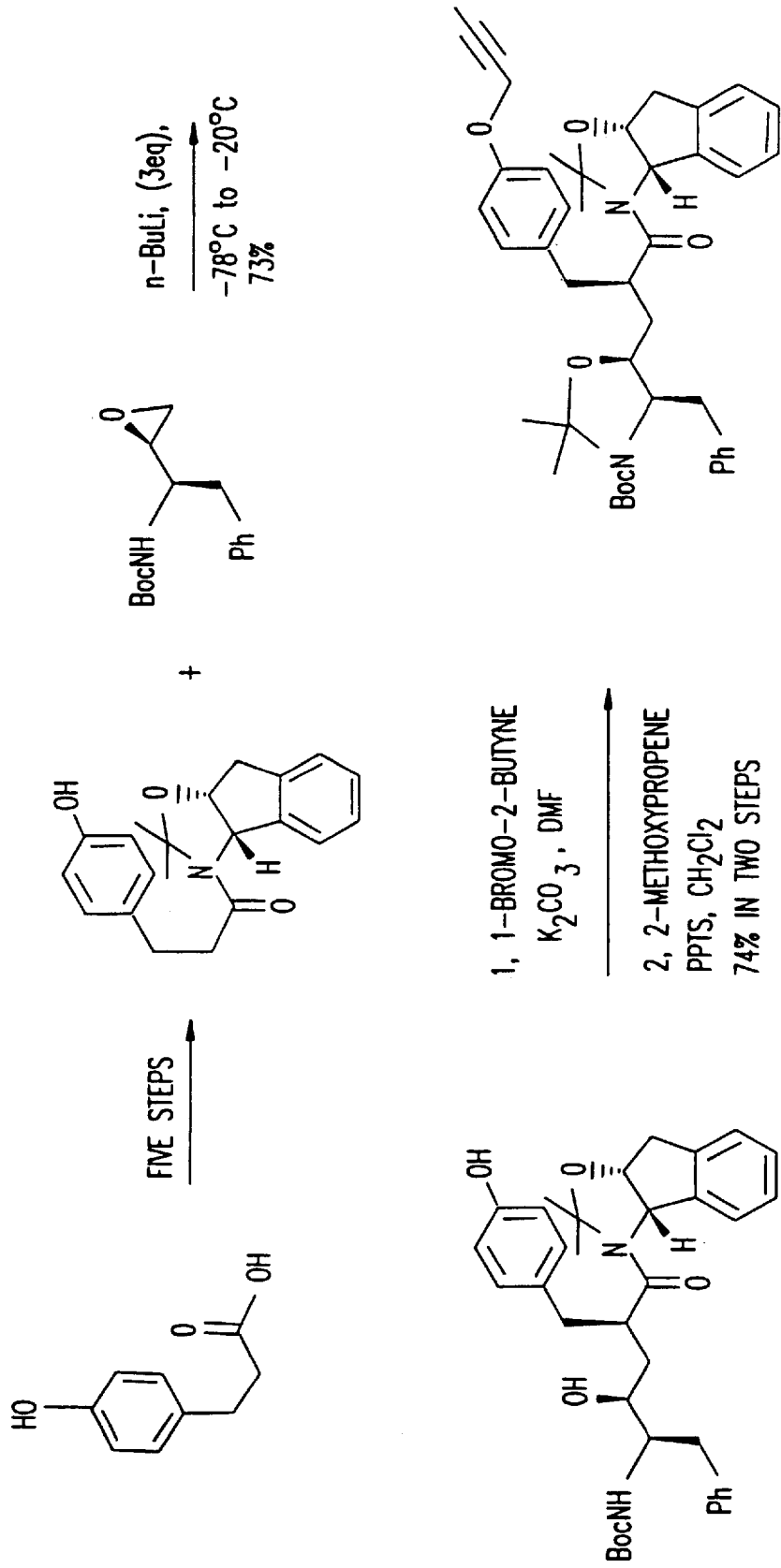
FIG. 8 depicts a coupling reaction useful for preparing compounds of the invention. (Askin, D, et al., J. Org. Chem. 1992, 57, 2771–2773).
Figure 9:
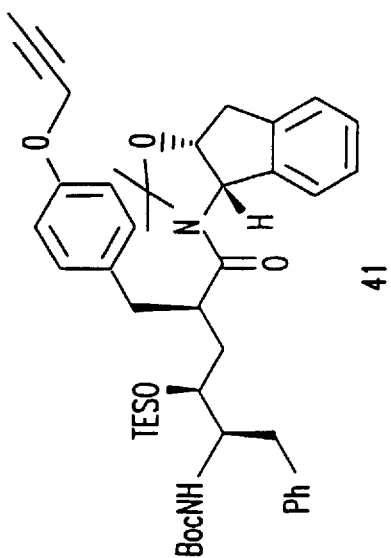
FIG. 9 depicts a reaction scheme in which an alkyne is converted to an α-diketone compound of the invention.
Figure 9:
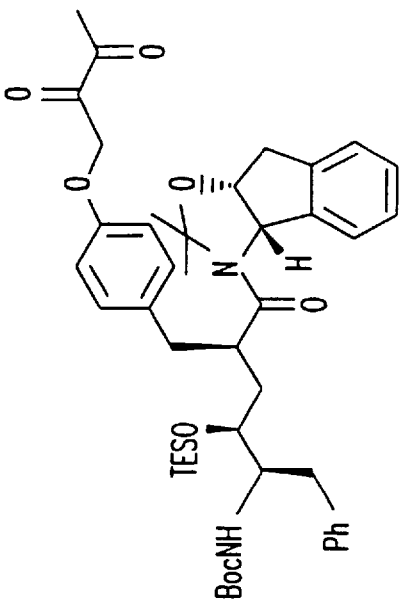
Figure 9:
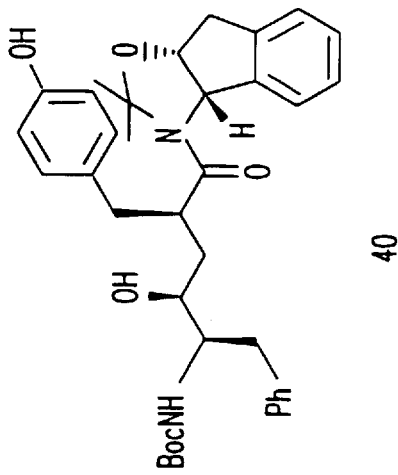

A coupling reaction useful for preparing compounds of the invention is shown in FIG. 8. The alkyne synthesized according to the above reaction scheme can then be converted to an α-diketone according to the reaction scheme shown in FIG. 9. A particularly preferred class of compounds according to the invention also can be synthesized according to the reaction scheme shown in FIG. 10.

The compounds of the invention have the following general formula:

wherein $R_A$ is $R_{A1}$, $OR_{A2}$, $NHR_{A2}$, where $R_{A1}$ is H, alkyl having 1 to about 12 carbon atoms or haloalkyl having 1 to about 12 carbon atoms and $R_{A2}$ is H or alkyl having 1 to about 12 carbon atoms; $R_B$ is a moiety that binds a protein; and x is 0 or 1.

In certain preferred embodiments, $R_B$ has one of the following formulas:

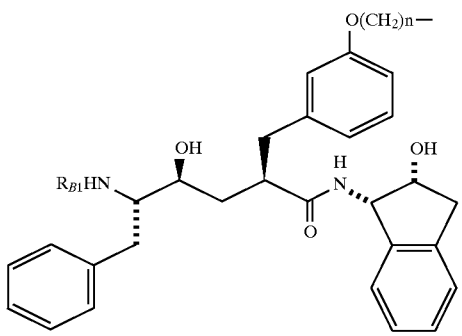

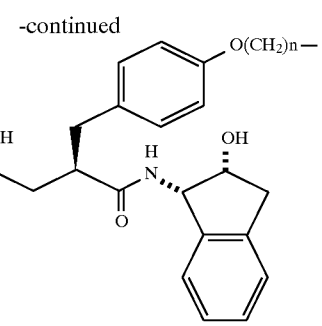

wherein $R_{B1}$ is H or an amine protecting group, and n is 1–10. A particularly preferred protecting group is the t-butyloxycarbonyl (Boc) group.

Where the compounds of the invention have more than one dicarbonyl group (i.e., where x=1) it is preferred that $R_B$ have the formula:

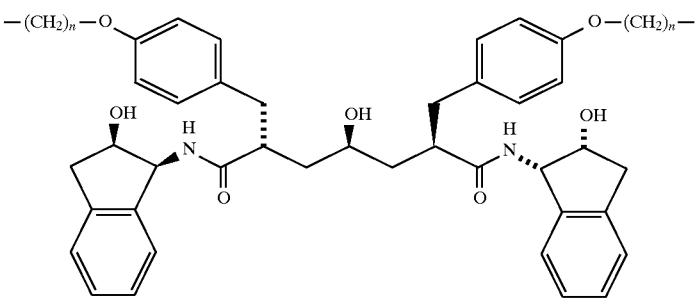

wherein n is 1–10.

The concept of irreversible enzyme inhibition is well established (See, e.g., Schaeffer, H. J., *Factors in the Design of Reversible and Irreversible Enzyme Inhibitors*, in Drug Design Vol. II, 129 (Academic Press, New York 1971); Baker, B. R., *Design of Active Site Directed Irreversible Enzyme Inhibitors* 122 (Wiley, New York 1967)), as is the concept of affinity labelling agents (Tipper, D.j. et al., *Proc. Natl. Acad. Sci.* USA 1965, 54, 1133). In general, irreversible inhibitors have a structure that is complementary to that of the target enzyme, and generally form one or more covalent bonds to an active site on said enzyme. It is thought that a reversible enzyme-inhibitor complex undergoes a transformation causing an enzyme to be irreversibly inhibited via covalent bond formation with the inhibitor.

The inventors have found that highly selective, reversible enzyme inhibitors can be produced by attaching α-dicarbonyl units to potent reversible enzyme inhibitors. Test results indicate that the novel compounds of the invention are highly selective for arginine containing proteins and peptides, in particular, HIV-1 protease. The design of the compounds of the invention minimizes the likelihood of either random covalent bond formation with other proteins, or reversal of the desired covalent bond formation. Another advantage of the inhibitors of the invention is that their high affinity, and selectivity for proteins with arginine residues facilitate the synthesis of proposed covalent inhibitors, whatever the enzyme target. The compounds of the invention should also have pharmacological activity associated with them as a result of their high selectivity for arginine-containing proteins and peptides. It is believed that irreversible inhibition will markedly increase the duration of enzyme inhibition.

The dicarbonyl moiety found in the compounds of the invention is capable of approaching within bonding distance of the arginine residue of a protein without interfering with the recognition of the inhibitor by the enzyme. Non-specific reaction of the α-dicarbonyl with other arginine containing molecules should no occur since we will employ selective, potent inhibitors. Moreover, the reaction between arginine and dicarbonyl compounds such as α-diketones and α-ketoaldehydes is relatively slow and somewhat reversible.

Although certain preferred embodiments of the invention incorporate an α-diketone moiety, the reactivity of the diketone functionality can be tuned by employing a variety of dicarbonyl moieties. For example, use of an α-ketoester or possibly α-ketoamide will decrease the electrophilicity of the resulting compound and should allow for increased selectivity in covalent bond formation, should this unexpectedly prove to be a problem. These two alternatives reduce the reactivity of the dicarbonyl unit by donating electron density, the amide more so that the ester. Conversely, employing, for example, an α-ketoaldehyde will increase the reactivity of the dicarbonyl moiety should this appear desirable.

It is contemplated that there can be random covalent bonding of the dicarbonyl containing targets of the invention with other proteins having exposed arginine residues. It is believed that the selectivity is derived from the attachment of a molecule that recognizes the targeted enzyme with a high specificity and potency. It is also believed to be important that the reaction of dicarbonyls with guanidine is a slow process, which should allow the enzyme to recognize the inhibitor before covalent bonding occurs. The high affinity of the inhibitor should anchor the dicarbonyl near the guanidine moiety long enough for the covalent bond to be able to form. The reversibility of the process also should allow any covalent bonds formed to undesired molecules to break while the desired covalent bonds should remain permanent again due to the affinity of the enzyme for the inhibitor.

The present invention also provides prophylactic, diagnostic, and therapeutic compositions comprising one or more of the compounds of the invention in a pharmaceutically acceptable diluent. By administering an effective amount of such compositions, for example, prophylactic or therapeutic responses can be produced in a human or some other type mammal. It will be appreciated that the production of prophylactic or therapeutic responses includes the initiation or enhancement of desirable responses, as well as the cessation or suppression of undesirable responses.

Compositions for use in the methods of this invention can be in the form of a solid, semisolid or liquid form and can include one or more of the compounds of the invention as an active ingredient in admixture with an organic or inorganic carrier or excipient suitable for external, internal, or parenteral applications. The active ingredient can be compounded, for example, with the usual non-toxic, pharmaceutically acceptable carriers for tablets, pellets, capsules, suppositories, solutions, emulsions, suspensions, and any other form suitable for use. The carriers that can be used are water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semisolid, or liquid form, and in addition, auxiliary, stabilizing, thickening, and coloring agents, and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin, and various like combinations thereof.

For parenteral administration, solutions of the compounds of the invention in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular, and subcutaneous injection purposes. The preparation of all these solutions under sterile conditions is readily accomplished by standard pharmaceutical techniques well-known to those skilled in the art. Additionally, it is possible to administer the compounds of the present invention topically when treating inflammatory conditions of the skin and this may preferably be done by way of creams, jellies, gels, pastes, ointments and the like, in accordance with standard pharmaceutical practice.

The amount of active ingredient that may be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. Persons skilled in the art can readily determine the appropriate amount of active ingredient and dosage from depending on the particular circumstances.

Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

Additional objects, advantages, and novel features of this invention will become apparent to those skilled in the art upon examination of the following examples thereof, which are not intended to be limiting.

General Experimental Procedures

All manipulations were conducted under an inert atmosphere (argon or nitrogen). All solvents were reagent grade.

Anhydrous ether, tetrahydrofuran (THF), benzene, and toluene were distilled from sodium and/or benzophenone ketyl. Dichloromethane ($CH_2Cl_2$) and was distilled from calcium hydride ($CaH_2$). N,N-Dimethylformamide (DMF) and acetonitrile were distilled from phosphorous pentoxide and calcium hydride. Methanol was distilled from magnesium and iodine. Organic acids and bases were reagent grade. Triethylamine, diisopropylethylamine, and N-methylmorpholine were distilled from calcium hydride. All the other reagents were commercial compounds of the highest purity available. Analytical thin-layer chromatography (TLC) was performed on Merck silica gel (60 F-254) plates (0.25 mm) precoated with a fluorescent indicator (0.50 mm plates were used for preparatory thin-layer chromatography). Visualization was effected using standard procedures unless otherwise stated. Flash column chromatography was carried out on Merck silica gel 60 particle size (0.040–0.063 mm). Melting points (mp) were determined with a Thomas-Hoover capillary melting point apparatus. Proton and carbon magnetic resonance spectra (1H-, 13C-NMR) were recorded on a Bruker AM-500 (500 MHz) Fourier transform spectrometer, and chemical shifts were expressed in parts per million (d) relative to tetramethylsilane (TMS-0 ppm) or $CHCl_3$ as an internal reference (7.24 ppm for $^1H$ and 77.0 ppm for $_{13}C$). Infrared spectra (IR) were obtained on a Perkin-Elmer Model 281-B or Perkin-Elmer Model 781 spectrometers. Absorptions are reported in wave numbers ($cm^{-1}$), and the spectra are calibrated against the 1601 $cm^{-1}$ band of a polystyrene film. Optical rotations (in degrees, °) were recorded on a Perkin-Elmer Model 241 polarimeter at the sodium D line. High resolution mass spectra (HRMS) were obtained on either a VG 70-70HS [a high resolution double focusing mass spectrometer using ammonia Chemical Ionization (CI) or Electron Impact (EI)] or a ZAB-E [using Fast Atom Bombardment (FAB), CI or EI]. Gas chromatograms were obtained on a Hewlett Packard 5890 GC incorporating a HP-1 Crosslinked Methyl Silicone Gum capillary column. Elemental analyses were Performed using conventional techniques.

EXAMPLE 1

Preparation of Compound 6 (FIG. 4)

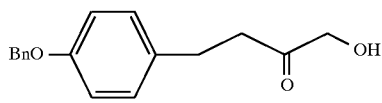

To a suspension of 1.66 g (20.0 mmol) 3-(4-hydroxyphenyl) propionic acid and 5.52 g $K_2CO_3$ in 20 ml DMF, 5.95 mn (50 mmol) benzyl bromide was added. The suspension was stirred overnight. After the reaction was complete, the reaction mixture was filtered, the filtrate was concentrated and treated with a solution of 599 mg LiOH in 20 ml dioxane, 10 ml of water, and THF, respectively. After the reaction was complete, the solution was concentrated and the residue diluted with water and extracted with $Et_2O$ (2×30 ml), the aqueous layer was acidified with iN HCl, extracted with $Et_2O$ (2×50 ml), the organic layer was then washed with 1N HCl, brine, dried over $Na_2SO_4$ to afford a pure product (5.05g) as a white solid in 98.6% yield: Rf=0.39 ($CH_2Cl_2/CH_3OH/AcOH$=9/1/0.05); mp 128°–130° C., HNMR (500 MHz, CDCl3) d 2.63 (t, J=8.02 Hz, 2H), 2.89 (t, j=7.58 Hz, 2H), 5.02 (s, 2H), 6.88–6.90 (m, 2H), 7.10–7.12 (m, 2H), 7.30–7.32 (m, 1H), 7.35–7.38 (m, 2H), 7.40–7.42 (m, 2H); $^{13}CNMR$ (125 MHz, $CDCl_3$) d 29.72, 38.84, 70.04, 114.94, 127.42, 127.88, 128.53, 129.22, 132.51, 137.09, 157.38, 179.24.

EXAMPLE 2

Preparation Unprotected Alkyne Interimediate

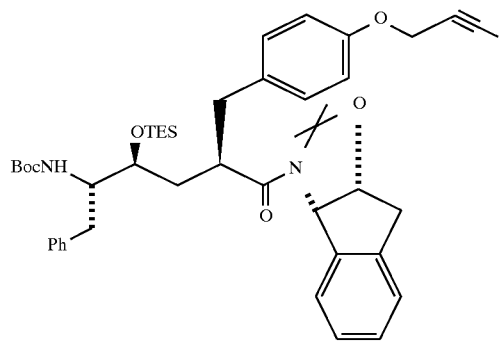

To a suspension of 167.1 mg of compound 40 (FIG. 9) and 115.5 mg $K_2CO_3$ in 2.8 ml DMF, 54.9 mg 2-butyn-bromide was added at room temperature. The mixture was stirred overnight. After the reaction was complete, the reaction mixture was diluted in 10 ml EtOAc and 3 ml $H_2O$, the aqueous layer was extracted with EtOAC (2×5 ml). The combined organic layer was washed with brine, dried over $Na_2SO_4$. Purified by flash chromatography over silica gel with Hexane/EtOAC (2.5/1) to give a pure material 171.4 mg in 96.2% yield: Rf=0.25 Hexane/EtOAC (2.5/1); [a]22D=+29.02 (C=0.61, $CHCl_3$); mp 76°–78° C.; 1HNMR (500 MHz, $CDCl_3$) d 1.28 (s, 3H), 1.33 (s, 1H), 1.40 (s, 9H), 1.48 (s, 3H), 1.72–1.74 (m, 2H), 1.79 (s, 3H), 2.63 (d, J=8.4 Hz, 1H), 2.89–2.99 (m, 2H), 3.03 (m, 2H), 3.24–3.33 (m, 2H), 3.55 (d, J=6.23 Hz, 1H), 3.71 (m, 1H), 4.60–4.65 (m, 2H), 4.70 (bs, 1H), 5.58 (bs, 1H), 6.22 (bs, 1H), 6.86 (d, J=7.92 Hz, 2H), 6.92–6.93 (m, 1H), 7.07 (d, J=7.75 Hz, 2H), 7.14–7.18 (m, 2H); 7.24–7.25 (m, 4H), 7.29–7.32 (m, 2H); 13CNMR (125 MHz, CDCl3) d major 3.6, 24, 26.41, 28.28, 36.11, 37.29, 38.11, 38.38, 44.13, 56.32, 56.43, 57.30, 65.58, 67.95, 74.12, 79.06, 83.67, 96.66, 114.94, 124.05, 125.46, 126.52, 127.06, 128.08, 128.43, 128.58, 129.34, 129.83, 130.29, 132.24, 138.25, 140.28, 156.65, 172.84; HR-FAB-MS m/z 653.3619 (M+H calcd for C40H48N2O6, 653.3590, 5 ppm err).

EXAMPLE 3

Preparation of Protected Alkyne Intermediate

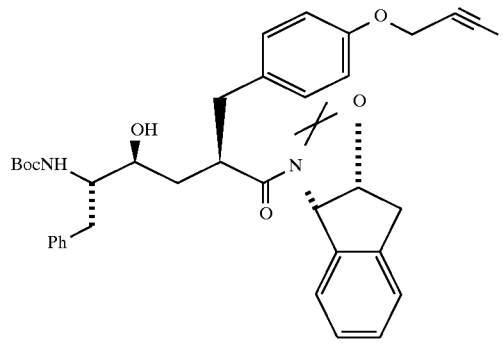

To a solution of 135.9 mg (0.2084 mmol) of the compound prepared according to Example 2 and 311.7 mg (4.58 mmol) imidazole in 0.6 ml DMF, 314.7 mg (2.08 mmol) TES-Cl was added at 0° C., warmed to room temperature and stirred for three hours. The reaction mixture was then diluted with $H_2O$ (1ml), and EtOAc (3ml). The aqueous layer was then extracted with EtOAc (2×2 ml), washed with 2.5% citric acid, brine and dried over Na₂SO₄. Purified by flash chromatograph over silica gel with Hexane/EtOAC (7/1) to give a pure white solid 148.1 mg in 89.5% yield: Rf=0.26 Hexane/EtOAc (6/1); mp 52°–54° C.; [a]22D=+16.15 (c=1.95, CHCl3); 1HNMR (500 MHz, CDCl₃) d 0.7 (q, J=7.88 Hz, 1H), 0.95 (t, J=3.9 Hz, 9H), 1.24 (s, 3H), 1.37 (s, 9H), 1.58 (s, 3H), 1.61–1.67 (m, 1H), 1.78 (t, J=2.19 Hz, 3H), 1.81–1.85 (m. 1H), 2.25 (dd, J=1.07, 1.86 Hz, 1H), 2.59 (t, J=11.07 Hz, 1H), 2.69 (dd, J=3.33, 9.95 Hz, 1H), 2.81 (dd, J=4.7, 8.6 Hz, 1H), 2.97 (d, J=16.79 Hz, 1H), 3.09 (dd, J=3.97, 16.79 Hz, 1H), 3.22 (dd, J=10.72, 12.76 Hz, 1H), 3.81–3.85 (m, 2H), 4.64 (m, 2H), 4.74 (t, J=4.15 Hz, 1H), 5.04 (d, J=9.73 HZ, 1H), 5.35 (d, J=4.23 Hz, 1H), 5.6 (d, J=7.66 Hz, 1H), 6.76–6.96(m, 5H), 7.08–19 (m, 4H), 7.22 (m, 3H), 7.35 (m, 1H); 13CNMR (125 MHz, CDCl3) d major 3.55, 5.38, 6.98, 23.97, 26.38, 28.32, 35.56, 36.11, 37.98, 39.46, 45.16, 54.0, 56.29, 64.99, 69.09, 74.18, 79.12, 79.46, 83.67, 96.33, 114.78, 124.12, 125.15, 126.43, 126.87, 127.82, 128.77, 129.2, 130.57, 132.64, 138.36, 140.3, 140.37, 155.79, 156. 57, 170.77. Anal. calcd. for C₄₆H₆₂N₂O₆Si: C, 72.02; H, 8.15; N, 3.65. Found: C, 71.89; H, 8.05; N, 3.56.

EXAMPLE 4

Conversion of Alkyne (41) to α-Diketone (42)

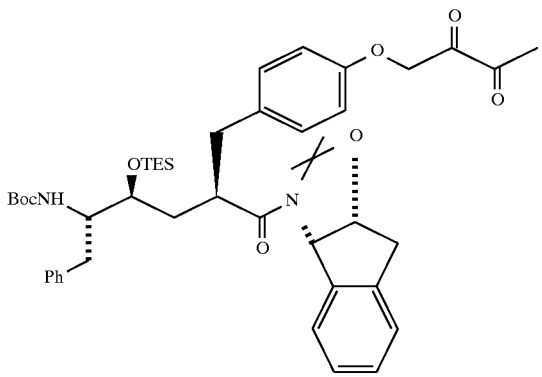

62 mg (0.07808 mmol) of the compound prepared according to Example 3 was dissolved in 1.69 ml mixture solvent CH₃CN/CCl₄/H₂O(1/1/1.5), and vigorously stirred until two clear layers appeared. The catalytic amount of RuO₂·H₂O was added. The solution was stirred for about 15 minutes. The reaction mixture was diluted in H₂O (2 ml), extracted with CH₂Cl₂ (2×5ml), dried over Na₂SO₄. Purified by flash chromatography over a very short silica gel column with Hexane/EtOAC (3/1) to afford a pure material 27.8 mg in 43.1% yield: Rf=0.23 Hexane/EtOAc (4/1); mp 60-2C; [a]22D=+20.14 (C=0.705, CH2Cl2); 1H NMR (500 MHz, CDCl₃) d 0.69 (q, J=7.85 Hz, 6H), 0.95 (s, 1H), 1.02 (t, J=7.82 Hz, 9H), 1.24 (s, 3H), 1.37 (s, 9H), 1.58 (s, 3H), 1.61–1.67 (m, 1H), 1.84 (m, 1H), 2.2–2.26 (m, 1H), 2.4 (s, 3H), 2.6–2.66 (m, 1H), 2.68–2.75 (m, 1H), 2.79–2.83 (m, 1H), 3.0 (s, 1H), 3.08–3.11 (m, 1H), 3.21–3.23 (m, 1H), 3.82–3.84 (m, 2H), 4.74–4.75 (m, 1H), 5.04–5.05 (m, 1H), 5.13 (s, 2H), 5.33 (d, J=3.72 Hz, 1H), 5.66 (d, J=7.10 Hz, 1H), 6.79–6.80 (m, 3H), 7.11–7.15 (m, 4H), 7.22–7.38 (m, 4H), 7.36 (m, 1H); 13C NMR (125 MHz, CDCl3) d 5.43, 7.03, 23.91, 26.47, 28.37, 35.54, 36.16, 37.99, 39.49, 45.04, 54.09, 65.00, 69.08, 69.35, 77.27, 79.21, 79.48, 96.41, 114.77, 123.99, 125.35, 126.48, 126.77, 127.97, 128.82, 129 (26), 130.93, 133.52, 138.43, 140.37, 140.47, 155.84, 156.56, 170.73, 192.55, 196.98.

EXAMPLE 5

Preparation of Unprotected Alkyne Intermediate

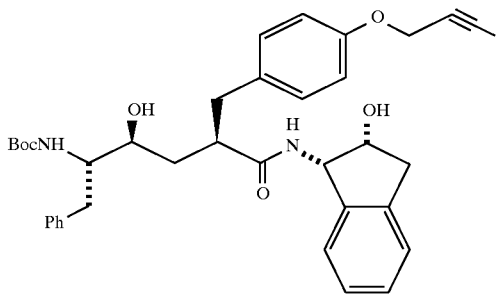

To a suspension of 204 mg (0.3643 mmol) N-(2(R)-Hydroxy-1 (S)-indanyl)-5(S)-[tert-butyloxycarbonyl) amino]-4(S)-hydroxy-6-(4-hydroxyphenyl)-2-(R) -[(4-hydroxyphenyl)methyl]hexanamide and 296.7 mg (0.9107 mmol, 2.5 eq) Cs₂CO₃ in 28.0 ml dioxane, 480.7 mg (3.64 mmol, 10 eq) 2-butyn-bromide was added. The mixture was heated at 72° C. and stirred overnight (~17.0 hr). The reaction mixture was filtered. The filtrate was evaporated and purified by flash chromatography over silica with CH₂Cl₂/CH₃OH (9/0.3) to give a pure material: 214.3 mg in 95.7% yield: Rf=0.24 CH₂Cl₂/CH₃OH (9/0.6); mp 205°–207°C.; [a]22D=+9.02 (c=0.61, DMSO); IR; 1HNMR (500 MHz, CDCl3) d 1.28 (s, 9H), 1.34–1.38 (m, 1H), 1.73 (t, J=12.06 Hz, 1H), 1.83 (t, J=2.14 Hz, 3H), 2.53–2.60 (m, 2H), 2.76–2.70 (m, 2H), 2.86–2.90 (m, 2H), 3.0 (dd, J=4.48, 16.0 Hz, 1H), 3.6 (m, 2H), 4.2 (s, 1H), 4.68 (m, 3H), 4.78 (sm 1H), 5.14 (dd, J=4.93, 8.4, 1H), 6.43 (d, J=9.03, 1H), 6.85 (d, J=8.59 Hz, 2H), 7.04 (d, J=7.06 Hz, 1H), 7.10 (d, J=8.46 Hz, 2H),. 7.13–7.26 (m, 8H), 7.60 (d, J=8.64 Hz, 1H); 13CNMR (125 MHz, CDCl3) d; 3.12, 28.18, 35.33, 35.73, 38.04, 39.33, 44,0, 55.74, 56.29, 56.62, 68.93, 72.14, 74.93, 77.36, 83.27, 114.29, 124.15, 124.68, 125.68, 126.16, 127.03, 127.94, 128.99, 129.75, 132.41, 139.70, 140.59, 142.23, 155.32, 155.68, 174.65.

EXAMPLE 6

Preparation of Protected Alkyne Intermediate

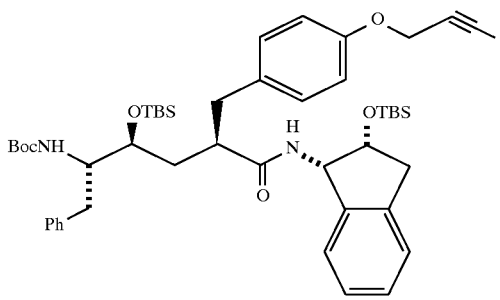

75.9 mg (0.124 mmol) of the compound prepared according to Example 5 and 185.5 mg (2.73 mmol, 22 eq) imidazole and 2.5 mg DMAP was dissolved in 0.8 ml DMF and cooled at 0° C. To the above solution, 186.9 mg (1.24 mmol, 10 eq) TBS-Cl was added. The reaction mixture was then warmed to room temperature and stirred for about three hours. The reaction mixture was treated with 0.5 ml CH₃OH for 30 minutes and diluted with 8 ml EtOAc and 2 ml 5% citric acid. The aqueous layer was extracted more with EtOAc (2×5 ml). The combined organic was washed with 5% citric acid, brine, and dried over Na₂SO₄. Purified by flash chromatography over silica gel with EtOAc/Hexane (1/5) to give a pure oil 87.2 mg in 83.68% yield. Rf=0.41 (EtOAc/Hexane (1/5)); [a]22D=+10 (c=1.19, CHCl3); 1HNMR (500 MHz, CDCl3) d; d −0.06 (s, 3H), −0.03 (s, 3H), 0.06 (s, 3H), 0.09 (s, 3H), 0.81 (s, 9H), 0.93 (s, 9H), 1.06 (s, 9H), 1.71–1.75 (m, 1H), 1.85 (t, J=2.3 Hz, 3H), 1.86–1.94 (m, 1H), 2.49 (dd, J=5.50, 13.6 Hz, 1H), 2.6–2.72 (m, 3H), 2.82 (d, J=17.26 Hz, 1H), 2.96 (dd, J=8.52, 13.6 Hz, 1H), 3.04 (dd, J=5.3, 16.24 Hz, 1H), 3.74 (dd, J=5.94, 7.87 Hz, 1H), 4.0 (dd, J=8.08, 16.24 Hz, 1H), 4.45–4.48 (m, 1H), 4.6 (m, 3H), 5.38 (dd, J=5.59, 8.62 Hz, 1H), 6.38 (d, J=8.78 Hz, 1H), 6.85 (d, J=8.58 Hz, 2H), 7.02 (d, J=8.51 Hz, 2H), 7.12–7.20 (m, 8H), 7.27–7.30 (m, 1H); 13CNMR (125 MHz, CDCl3) −4.88, −4.84, −4.34, −3.74, 3.70, 18.11, 18.20, 25.90, 25.60, 27.95, 36.57, 37.58, 38.20, 40.77, 45.95, 53.44, 56.28, 56.45, 70.73, 73.89, 74.20, 79.16, 83.45, 114.79, 124.52, 124.75, 126.28, 126.87, 127.43, 128.39, 129.02, 129.90, 132.62, 138.61, 139.70, 141.94, 155.81, 156.40, 174.64; IR (CHCl3) 3470 (m), 2960 (s), 2930(S), 2860 (m), 1700(s), 1665(m), 1605 (w), 1500 (s), 1250 (m), 1160 (m), 1070 (m), 100 (m), 935 (w), 830 (S); HR-FAB-MS m/z 841.5023 (M+H calcd for $C_{49}H_{72}N_2O_6Si_2$, 841.5006, 3ppm err) Anal. calcd for $C_{49}H_{72}N_2O_6Si_2$: C, 69.96; H, 8.63; N, 3.33.

EXAMPLE 7

Conversion of Protected Alkyne Into α-Diketone

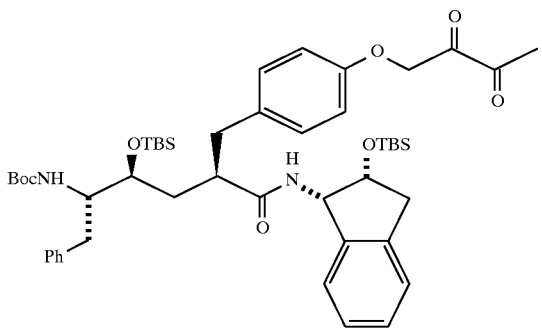

51.9 mg of the compound prepared according to Example 6 was dissolved in a mixture solvent CH₃CN/CCl₄/H₂O (1/1/1.5). The mixture was vigorously stirred until two clear layers appeared. Then the catalytic amount of RuO2. H2O was added. The solution was stirred for about 15 minutes. The reaction mixture was diluted in H₂O (2 ml), extracted with CH₂Cl₂ (2×5 ml), the organic layer was dried over Na₂SO₄. The crude material was then purified by flash chromatography over a very short silica gel column with EtOAc/Hexane (1/2.5) to give a pure product 43.5 mg in 80.7w yield: Rf=0.258 (Hexane/EtOAc 2.5/1); [a]22D=+8.5 (c=0.6, CHCl3); IR (CHCl3) 3440 (w), 2960 (m), 2930 (m), 2860 (m), 1700 (m), 1670 (m), 1500 (s), 1365 (w), 1250 (m), 1160 (m), 1085 (m), 1065 (m), 835 (s); 1HNMR (500 MHz, CDCl3) d −0.07 (s, 3H), −0.04 (s,3H), 0.06 (s,3H), 0.09 (s,3H), 0.8 (s,9H), 0.93 (s,9H), 1.06 (s,9H), 2.4 (s,3H), 2.47 (dd, J=5.51,13.48 Hz,1H), 2.58–2.66 (m,1H), 2.7(m,1H), 2.82 (d, J=16.25 Hz, 1H), 2.95 (dd, J=8.57,13.58 Hz,1H), 3.04 (dd, J=5.06,16.34 Hz, 1H), 3.75 (m,1H), 3.99 (m,1H), 4.45–4.47 (m, 1H), 4.60 (m, 1H), 5.1 (s, 2H), 5.37 (dd, J=5.52, 8.6 Hz), 6.39 (d, J=8.7Hz, 1H), 6.8 (m, 2H), 7.01 (d, J=8.5 Hz, 2H), 7.12–7.2 (m, 6H), 7.26–7.9 (m, 2H); 13CNMR (125 MHz, CDCl3) d 4.85, −4.33, −3.73, 18.11, 18.2, 23.86, 25.89, 25.99, 27.94, 29.68, 36.44, 37.58, 38.2, 40.77, 45.91, 53.39, 56.27, 69.27, 70.67, 73.87, 77.20, 79.20, 114.61, 114.79, 124.53, 124.73, 126.31, 126.87, 127.45, 128.41, 129.01, 130.14, 133.45, 138.60, 139.71, 141.90, 155.82, 156.16, 174.54, 192.44, 192.44, 196.94; HR-FAB-MS m/z 873.4891 (M+H calcd for $C_{49}H_{72}N_2O_8Si_2$, 873.4905, 1ppm err) Anal. calcd for C49H72N208Si2: C, 66.03; H, 8.38; N. 3.15. Found: C, 65.92; H, 8.36; N, 3.04.

EXAMPLE 8

Figure 10:
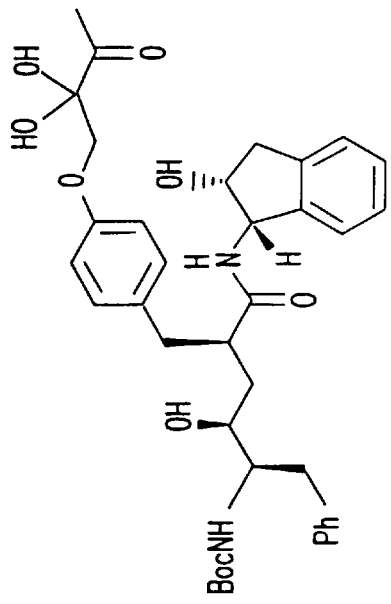
FIG. 10 depicts a reaction scheme for the synthesis of a preferred compound of the invention, 4 (discussed in example 9).
Figure 10:
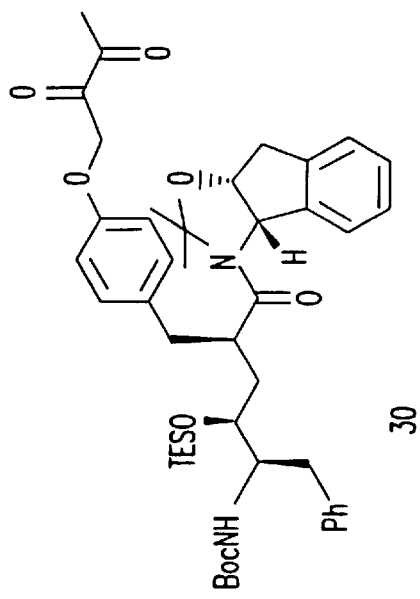
Figure 10:
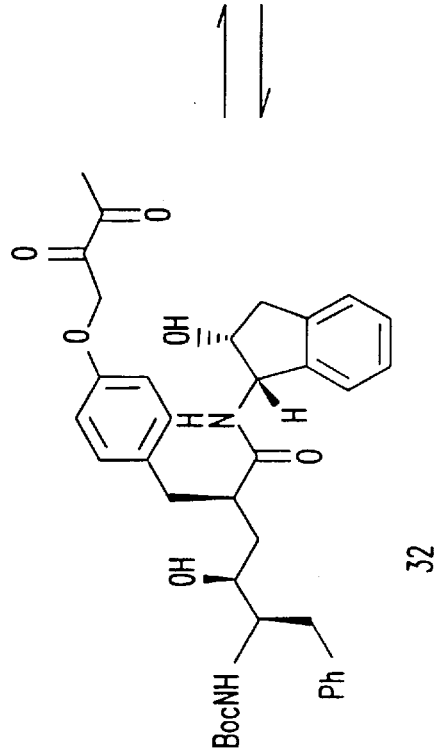

Preparation of Compound 32 (FIG. 10)

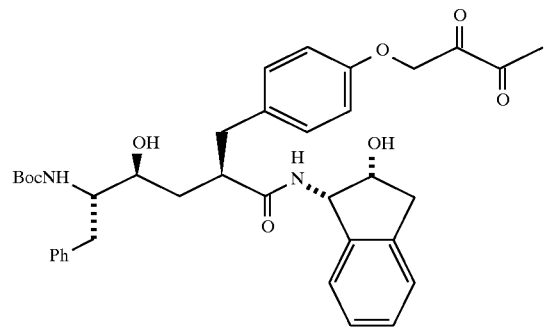

37.2 mg of the compound prepared according to Example 7 was dissolved in 4 ml of CH₃CN/H2O (1.5/1) was mixed with catalytic amount of CSA (0.2 eq) and heated at 42° C. overnight. After the reaction was complete, the reaction mixture was extracted with EtOAC (2×10 ml), washed with 2.5% NaHCO₃, brine, dried over Na₂SO₄. The crude material was then purified by semi-preparative RH-HPLC (condition: 21.4 C18 dynamic column, buffer A: 0.1% TFA in H2O, buffer B: 0.1% TFA in CH₃CN, Gradient 55–95% B over 25 minutes flow rate 12 ml/min., monitored at 276 nm) to give a pure product 20.1 mg in 80.39% yield: IR (KBr) 3400 (s), 2925 (m), 1720 (m), 1680 (s), 1510 (s), 1450 (w), 1390 (w), 1370 (m), 1250 (m), 1200 (m), 1170 (s), 1050 (m), 740 (w), 700 (w); 1HNMR (500 MHz, CDCl3) d 1.38 (s, 9H), 1.82–1.86 (m, 2H), 2.40 (s, 3H), 2.50–2.60 (m, 2H), 2.69–2.77 (m, 3H), 2.81–2.88 (m, 2H), 2.90–2.94 (m, 1H), 3.03 (dd, J=5.05, 16.7 Hz, 1H), 3.66–3.68 (m, 1H), 3.79 (m, 1H), 4.23 (t, J=4.85 Hz, 1H), 4.90 (d, J=8.24 Hz, 1H), 5.14 (s, 2H), 5.22 (dd, J=4.8, 8.39 Hz, 1H), 6.0 (d, J=8.85 Hz, 1H), 6.80 (d, J=8.41 Hz, 2H), 7.05–7.08 (m, 3H), 7.17–7.23 (m, 6H), 7.28–7.32 (m, 2H); 13CNMR (125 MHz, CD₃CN-D₂O) d (wy1218c5) 24.84, 28.52, 36.77, 38.14, 38.74, 39.90, 46.37, 57.20, 57.97, 70.07, 71.80, 73.67, 80.20, 95.56, 115.31, 115.53, 95.56, 115.31, 115.53, 116.04, 125.00, 126.08, 127.09, 127.70, 128.77, 129.24, 130.15, 131.07, 133.44, 139.89, 141.48, 157.50, 157.59, 177.56, 208.76; HR-FAB-MS m/z 645.3190 (M+H calcd for $C_{37}H_{44}N_2O_8$, 645.3175, 3ppm err)

EXAMPLE 9

Comparative Analysis

The biological activity compound (4) was compared with the known enzyme inhibitor (1) N-(2(R)-Hydroxy-1(S)-indonyl)-5(S)-[tert-butyloxycarbonyl)amino]-4(S)-hydroxy-6-(4-hydroxyphenyl)-2-(R) -[(4-hydroxyphenyl)methyl]hexanamide. See, e.g., Thompson, W. J. et al., *J. Med. Chem.* 1992, 35, 1685) according to methods recited in the Thompson, supra. and Heimbach, J. C. et al., *Biochem. Biophys. Res. Commun.* 1989, 164, 955–960.

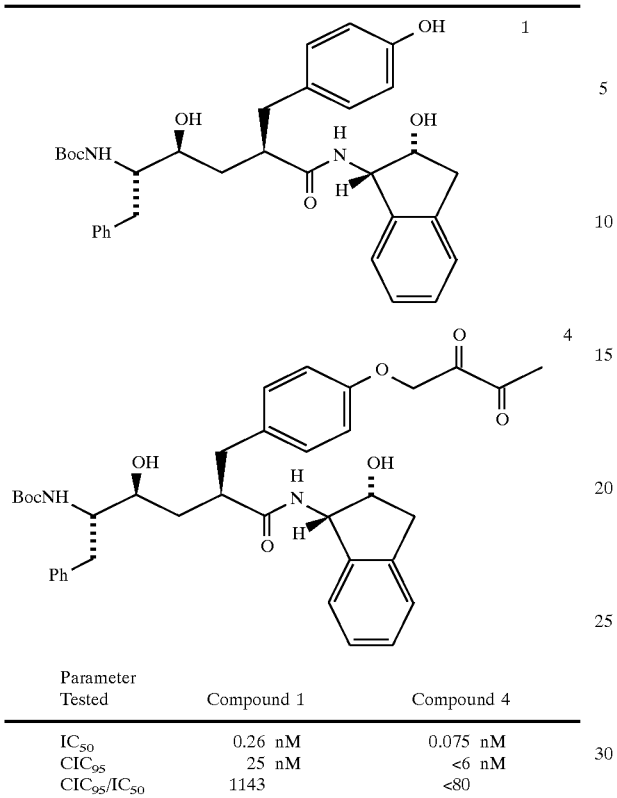

| Parameter Tested | Compound 1 | Compound 4 |
|---|---|---|
| $IC_{50}$ | 0.26 nM | 0.075 nM |
| $CIC_{95}$ | 25 nM | <6 nM |
| $CIC_{95}/IC_{50}$ | 1143 | <80 |

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the formula:

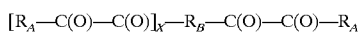

wherein:

$R_A$ is $R_{A1}$, $OR_{A2}$, $NHR_{A2}$, where $R_{A1}$ is H, alkyl having 1 to about 12 carbon atoms or haloalkyl having 1 to about 12 carbon atoms and $R_{A2}$ is H or alkyl having 1 to about 12 carbon atoms;

$R_B$ has the formula:

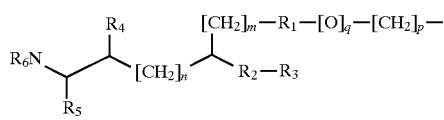

wherein:

$R_1$ is aryl having 5 to 14 carbon atoms;
$R_2$ and $R_3$ are defined such that:
(a) $R_2$ is C(O)—NH, —CH=CH—, a pyrrolinone ring, —SO$_2$—, —CH$_2$NH; and
$R_3$ is indolyl, aryl having about 5 to about 14 carbon atoms, or alkyl having 1 to about 12 carbon atoms; or
(b) $R_2$ is C(O); and
$R_3$ is NH—CH($R_7$)—C(O)OH wherein $R_7$ is an amino acid side chain;

$R_4$ is OH, —CH(OH)—, —CH(OH)CH(OH)—, CH$_2$NH—, —SO$_2$—, or —C(O) CF$_2$;
$R_5$ is aryl having about 5 to about 14 carbon atoms or an amino acid side chain;
$R_6$ is an amine protecting group or has the structure $R_8$—C(O)— wherein $R_8$ is alkyl having 1 to about 12 carbon atoms or aryl having 5 to 14 carbon atoms;
n is 1–5;
m is 1–10;
q is 0 or 1;
p is 1–10; and
x is 0 or 1.

2. The compound of claim 1 wherein $R_A$ is CH$_3$ or CF$_3$.

3. The compound of claim 1 wherein $R_B$ has the formula:

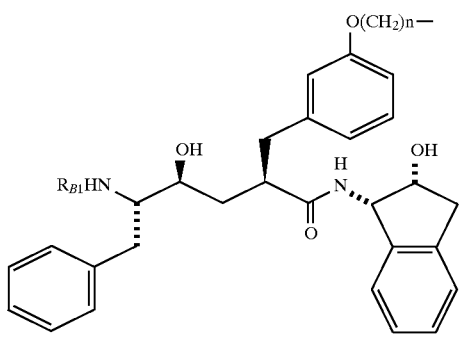

$R_{B1}$ is H or an amine protecting group, x is 0; and n is 1–10.

4. The compound of claim 1 wherein $R_B$ has the formula:

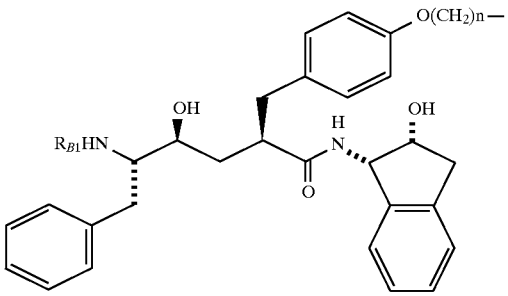

$R_{B1}$ is H or an amine protecting group; x is 0; and n is 1–10.

5. The compound of claim 1 wherein $R_B$ has the formula:

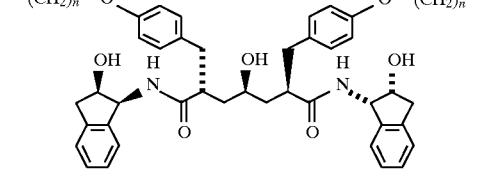

X is 1; and n is 1–10.

6. A composition comprising the compound of claim 1 in a pharmaceutically acceptable carrier.

7. A method for treating HIV by inhibiting the chemical or biological activity of an arginine-containing protein, comprising contacting said protein with a compound having formula:

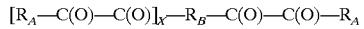

wherein:

$R_A$ is $R_{A1}$, $OR_{A2}$, $NHR_{A2}$, where $R_{A1}$ is H, alkyl having 1 to about 12 carbon atoms or haloalkyl having 1 to about 12 carbon atoms and $R_{A2}$ is H or alkyl having 1 to about 12 carbon atoms;

$R_B$ has the formula:

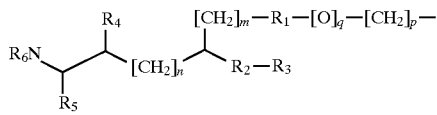

wherein:

$R_1$ is aryl having 5 to 14 carbon atoms;

$R_2$ and $R_3$ are defined such that:
(a) $R_2$ is C(O)—NH, —CH=CH—, a pyrrolinone ring, —SO$_2$—, —CH$_2$NH; and
  $R_3$ is indolyl, aryl having about 5 to about 14 carbon atoms, or alkyl having 1 to about 12 carbon atoms; or
(b) $R_2$ is C(O); and
  $R_3$ is NH—CH($R_7$)—C(O)OH wherein $R_7$ is an amino acid side chain;

$R_4$ is OH, —CH(OH)—, —CH(OH)CH(OH)—, CH$_2$NH—, —SO$_2$—, or —C(O) CF$_2$;

$R_5$ is aryl having about 5 to about 14 carbon atoms or an amino acid side chain;

$R_6$ is an amine protecting group or has the structure $R_8$—C(O)- wherein $R_8$ is alkyl having 1 to about 12 carbon atoms or aryl having 5 to 14 carbon atoms;

n is 1–5;

m is 1–10;

q is 0 or 1;

p is 1–10; and x is 0 or 1.

8. The method of claim 2 wherein said protein is an enzyme.

9. The method of claim 8 wherein said enzyme is an aspartic acid proteolytic enzyme.

10. The method of claim 8 wherein said enzyme is a protease.

11. The method of claim 8 wherein said enzyme is a protease associated with human immunodeficiency virus.

12. The method of claim 8 wherein said enzyme is HIV-1 protease.

13. The method of claim 7 wherein said moiety $R_B$ covalently bonds with said protein.

14. The method of claim 8 wherein said moiety $R_B$ hydrogen bonds with said protein.

* * * * *